(12) United States Patent
Ryan et al.

(10) Patent No.: US 10,557,775 B2
(45) Date of Patent: Feb. 11, 2020

(54) SYSTEM FOR GENERATING DATA RELATING TO A TISSUE CORE BIOPSY, AND THE USE OF THE SYSTEM TO DETECT TISSUE ABNORMALITIES, IN PARTICULAR CANCEROUS TISSUE, IN A PATIENT

(71) Applicant: Maximillian Frederick Ryan, County Cork (IE)

(72) Inventors: Maximillian Frederick Ryan, County Cork (IE); Len McCarthy, County Cork (IE)

(73) Assignee: DIOPSY LIMITED, County Cork (IE)

( * ) Notice: Subject to any disclaimer, the term of this patent is extended or adjusted under 35 U.S.C. 154(b) by 162 days.

(21) Appl. No.: 15/564,016

(22) PCT Filed: Apr. 4, 2016

(86) PCT No.: PCT/EP2016/057354
§ 371 (c)(1),
(2) Date: Oct. 3, 2017

(87) PCT Pub. No.: WO2016/156615
PCT Pub. Date: Oct. 6, 2016

(65) Prior Publication Data
US 2018/0136091 A1    May 17, 2018

(30) Foreign Application Priority Data

Apr. 3, 2015   (EP) ..................................... 15248043

(51) Int. Cl.
*G01N 1/08* (2006.01)
*H01J 49/26* (2006.01)
(Continued)

(52) U.S. Cl.
CPC ................ *G01N 1/08* (2013.01); *B01L 3/502* (2013.01); *G01N 1/40* (2013.01); *G01N 33/50* (2013.01);
(Continued)

(58) Field of Classification Search
CPC ....... G01N 1/08; B01L 3/502; A61B 10/0275; A61B 10/0283; A61B 2010/0225
See application file for complete search history.

(56) References Cited

U.S. PATENT DOCUMENTS

| 2011/0215233 | A1 | 9/2011 | Vertes Akos et al. |
| 2012/0156712 | A1* | 6/2012 | Takats ...................... G01N 1/02 435/29 |
| 2014/0257135 | A1* | 9/2014 | DeFreitas .......... A61B 10/0275 600/566 |

FOREIGN PATENT DOCUMENTS

| GB | 2 491 486 | 12/2012 |
| WO | WO 2010/136887 | 12/2010 |

\* cited by examiner

*Primary Examiner* — Christopher Adam Hixson
(74) *Attorney, Agent, or Firm* — Cesari and McKenna, LLP

(57) ABSTRACT

A system for generating data relating to a tissue core comprises a core needle biopsy module configured to obtain a tissue core from a locus within the body, and a tissue disintegration module operably connected to the core needle biopsy module and configured to receive a tissue core from the core needle biopsy module and convert at least a portion of the tissue core into gaseous tissue molecules. The system also comprises first vacuum pump means configured to convey a tissue core from the needle biopsy module to the tissue disintegration module, and second vacuum pump means configured to convey gaseous tissue molecules from the tissue disintegration module to an analyser module.

9 Claims, 10 Drawing Sheets

(51) Int. Cl.
   *G01N 33/50*    (2006.01)
   *B01L 3/00*     (2006.01)
   *G01N 1/40*     (2006.01)
   *A61B 10/02*    (2006.01)
   *A61B 90/00*    (2016.01)

(52) U.S. Cl.
   CPC ........... *H01J 49/26* (2013.01); *A61B 10/0233* (2013.01); *A61B 90/39* (2016.02); *A61B 2010/0225* (2013.01); *B01L 2200/025* (2013.01); *B01L 2400/049* (2013.01); *G01N 2001/4038* (2013.01)

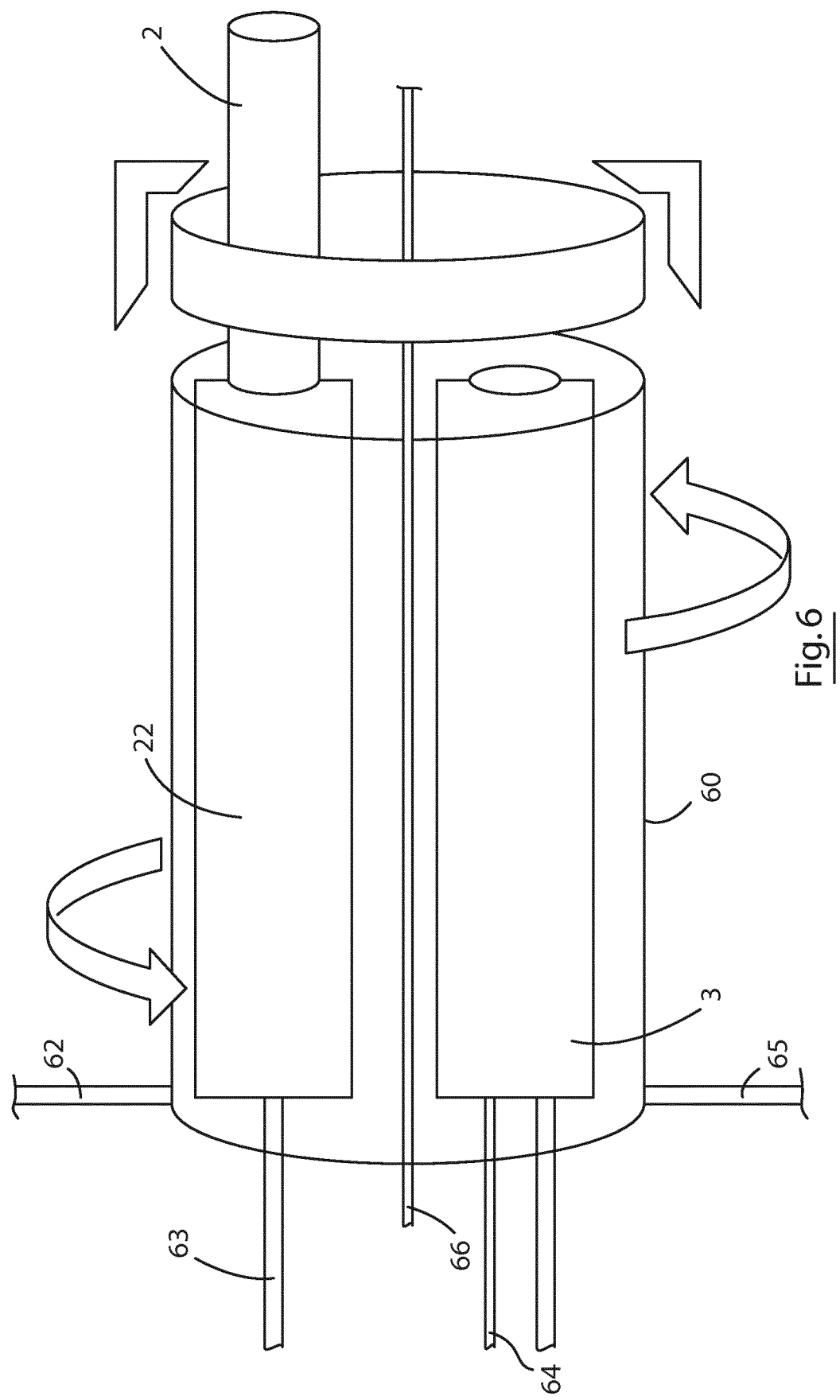

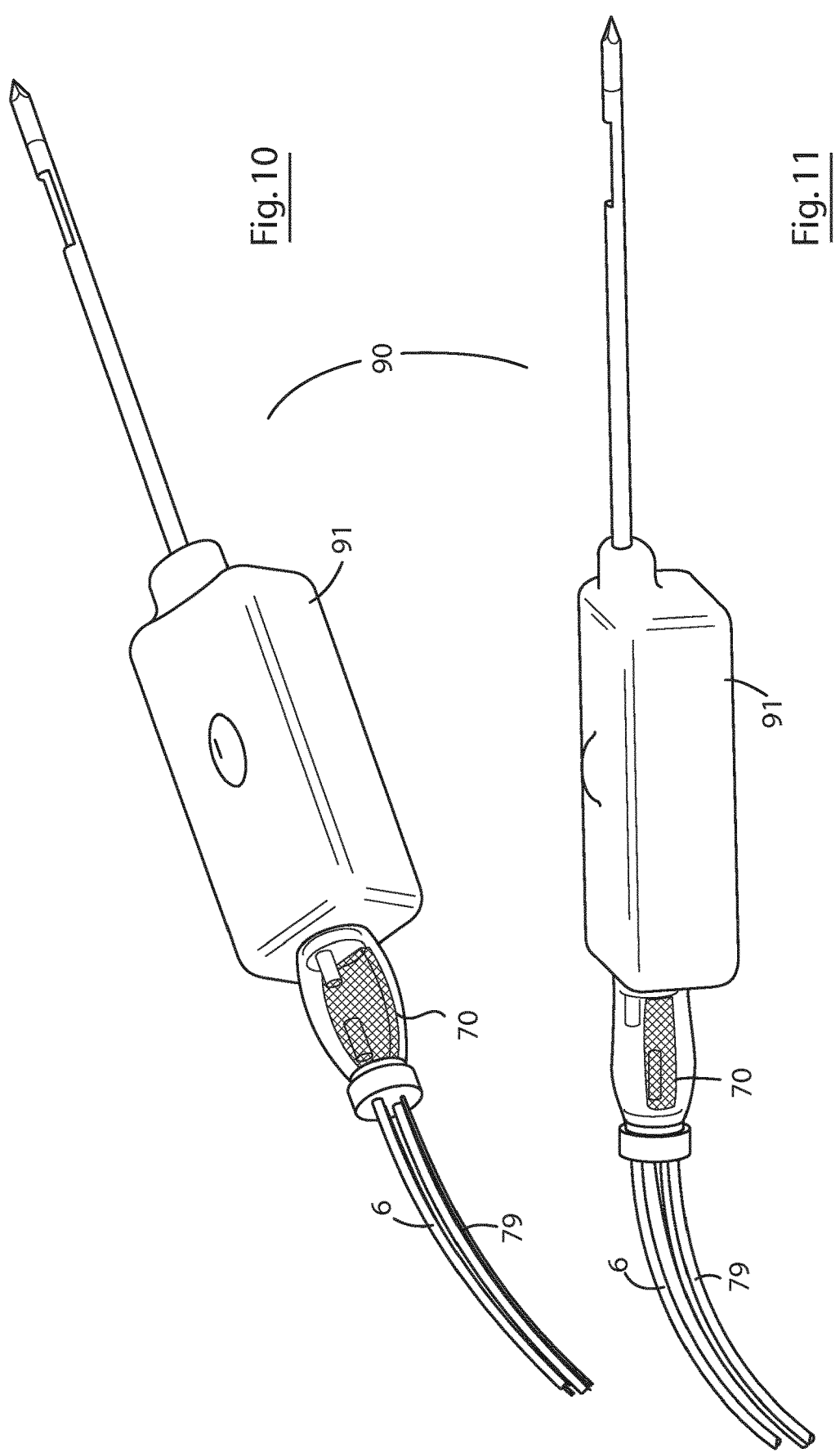

SYSTEM FOR GENERATING DATA RELATING TO A TISSUE CORE BIOPSY, AND THE USE OF THE SYSTEM TO DETECT TISSUE ABNORMALITIES, IN PARTICULAR CANCEROUS TISSUE, IN A PATIENT

CROSS REFERENCE TO RELATED APPLICATIONS

This application is the National Stage of International Application No. PCT/EP2016/057354, filed on Apr. 4, 2016, which claims the benefit of European Application No. 15248043.0, filed on Apr. 3, 2015. The contents of both applications are hereby incorporated by reference in their entirety.

TECHNICAL FIELD

The invention relates to systems for generating data relating to tissue core biopsies. In particular, the invention relates to systems for generating data relating to a patients cancer status, and methods for detecting cancer in patients.

BACKGROUND TO THE INVENTION

Breast cancer continues to affect approximately one woman in ten in the western world and despite the phenomenal advances in recent years the mortality rate is as high as 35%. Diagnosis of breast cancer generally involves a triple assessment process, which includes a visit to a clinic or hospital for assessment for a clinical assessment and examination, radiology imaging tests and a core needle biopsy and or Fine needle aspiration biopsy to be taken, and subsequent analysis of the biopsy by a Histopathologist or Cytologist.

Tissue core biopsies are taken using a needle punch device. The device generally comprises a needle having a hollow core and a retractable sheath. Some needle biopsy systems include a vacuum pump in fluid communication with the hollow core of the needle. In use, the device is inserted into the breast and the needle tip generally inserted into a mass within the breast with the aide of ultrasound and less frequently mammography and magnetic resonance imaging. Once in situ, retraction of the sheath causes adjacent tissue to herniate into the hollow core of the needle, whereby extension of the sheath cuts the tissue leaving a sequestered core within the needle, which is withdrawn, by the action of the vacuum pump into a collection chamber. Generally, the needle is capable of rotation about its longitudinal axis, allowing a circumferential series of core needle biopsy samples to be obtained at a desired locus. In the case of mammographic biopsies, these are usually obtained using stereotactic guidance. The core biopsies thus obtained maybe analysed by a radiologist for the presence of microcalcifications within the sequestered core biopsy samples, prior to being sent to a pathology laboratory for histological analysis by a pathologist.

The core needle biopsy device may also include a conduit for delivering variable amounts of local anaesthetic and placing a localization marker to the said sequestered outlets for delivery to the site of the extruded longitudinal strips of core biopsy tissue product and/or tissue material product.

As the histological analysis process may take several days to complete after the biopsy is taken, this necessitates that the patient has to make a first visit to the clinic or hospital for a biopsy to be taken, and a second visit to meet with the clinician to receive the diagnosis. In some cases, if the biopsy taken from the margin or satellite tissue is determined to be cancerous, further hospital visits maybe required for additional radiology imaging tests and further core biopsy needle biopsy tissue samples to be taken. It is one object of the invention to overcome at least one of these problems.

The IKNIFE is a surgical tool that helps surgeons detect cancer in a patient in real time while the patient is undergoing surgery. The IKNIFE comprises a surgical knife having a heating element that is capable of converting tissue to gaseous tissue molecules (ionization), a mass spectrometer, and a vacuum pump and conduit configured to convey the ionized tissue to the mass spectrometer where the gaseous ions are analysed to determine whether the tissue is cancerous. The device is used during surgery to resect tumours, and in particular to cut away margins and simultaneously determine in real time whether the margins are cancerous or not. The IKNIFE device is described in WO2010136887. Methods for subcellular analysis by laser ablation electrospray mass spectrometry are described in US2011/0215233. Methods for analysis of non-living substrates using an electrosurgical knife to generate ions and a mass spectrometer to analyse the ions is described in GB2491486.

STATEMENTS OF INVENTION

The Applicants have discovered that the underlying concept of the IKNIFE can be translated into a needle biopsy device and employed to provide real time diagnostic information to a clinician during a core needle biopsy procedure, thus allowing a clinician to tailor the biopsy procedure, avoid having to take excessive number of biopsies, and provide the patient with an initial diagnosis immediately after the procedure. The invention relates to a system comprising a needle biopsy module, a tissue disintegration module operatively linked to the needle biopsy module for receipt of a tissue core from the needle biopsy module, and optionally an analyser operatively linked to the disintegration module for receipt of gaseous tissue molecules from the disintegration module. In a first embodiment, the system is provided as a "plug-and-play" system in which the tissue disintegration module is removably attached to the needle biopsy module and can be easily detached and replaced with a removable tissue core collection module adapted to collects tissue cores for further analysis. In this embodiment, the system can be adapted to analyse gaseous molecules generated from tissue cores by means of mass spectrometry or NMR, or collect tissue cores for analysis by other means for example histology or cytology. In a different, but linked embodiment, the system can comprise both tissue disintegration and tissue collection modules, and adjustment means for alternatively aligning either the tissue disintegration module or tissue collection module with the needle biopsy module for receipt of a tissue core.

Thus, in a first aspect, the invention provides a system for generating data relating to a tissue core, comprising:
- a core needle biopsy module configured to obtain a tissue core from a locus within the body;
- a tissue disintegration module operably connected to the core needle biopsy module and configured to receive a tissue core from the core needle biopsy module and convert at least a portion of the tissue core into gaseous tissue molecules; and
- a conveying module operable to convey a tissue core from the needle biopsy module to the tissue disintegration module and/or convey gaseous tissue molecules from the tissue disintegration module to an analyser module.

In one embodiment, the system comprises an analyser module. In one embodiment, the analyser module is operably connected to the conveying module for receipt of the gaseous tissue molecules from the disintegration module. In one embodiment, the analyser module is configured to analyse the gaseous tissue chemicals or molecules, and generate data relating to the tissue core based on the gaseous tissue molecules.

In one embodiment, the analyser module comprises a mass spectrometer. However, other analysers are envisaged such as for example nuclear magnetic resonance spectroscopy or gas chromatography.

In one embodiment, the core needle biopsy module and tissue disintegration module are provided as a single unit, and wherein the tissue disintegration module is removably attached to the core needle biopsy module. In one embodiment, the system comprises a tissue core collection module configured for removable attachment to the core needle biopsy module in place of the tissue disintegration module for collection of one or more tissue cores from the core needle biopsy module. This allow the system to be used in a disintegration mode where one or more cores are optionally converted to gaseous molecules which are analysed by for example mass spectrometry, and then typically adapted to a core collection mode where obtained cores are collected for subsequent analysis intact (i.e. by means of cytology or histology) by removing the tissue disintegration module and replacing it with the tissue collection module.

In another embodiment, the system comprises a tissue core collection module, wherein the tissue disintegration module, the core needle biopsy module, and the tissue core collection module are typically provided as a single unit, wherein the unit is generally adjustable from a first configuration in which the tissue disintegration module is aligned with the core needle biopsy module for receipt of a tissue core therefrom to a second configuration in which the tissue core collection module is aligned with the core needle biopsy module for receipt of a tissue core therefrom.

In one embodiment, the unit comprises adjustment means for aligning the core needle biopsy module with different modules, for example, the tissue core collection module and the tissue disintegration module. In one embodiment, the tissue core collection module and the tissue disintegration module are provided on a first rotor configured for rotation from at least the first configuration to at least the second configuration.

In one embodiment, the tissue core collection module and the tissue disintegration module are contained within a single chamber. In one embodiment, the conveying module comprises a vacuum pump. In one embodiment, the single chamber is in fluid communication with the vacuum pump for evacuation of the chamber.

In one embodiment, the conveying module comprises a pump (i.e. a vacuum pump) and associated conduits. In one embodiment, the conveying module comprises a first conveying module configured to convey a tissue core from the needle biopsy module to the tissue disintegration module and second conveying module configured to convey gaseous tissue molecules from the tissue disintegration module to an analyser module. In one embodiment, the first and second conveying modules share a single pump. In another embodiment, the first and second conveying modules have separate pumps.

In one embodiment, the first conveying module comprises a vacuum pump and a first conduit providing fluid communication between the vacuum pump and the tissue disintegration module. Thus, when the vacuum pump is actuated, and when the tissue disintegration module is operably connected (i.e. aligned) with the needle biopsy module, negative pressure is typically generated in the tissue disintegration module causing any core in the needle biopsy module to be withdrawn into the tissue disintegration module.

In one embodiment, the second conveying module comprises a vacuum pump operably connected to a second conduit providing fluid communication between an analyser and the tissue disintegration module. Thus, when the vacuum pump is actuated, negative pressure is typically generated in the tissue disintegration module causing any gaseous molecules in the tissue disintegration module to be withdrawn into the analyser module through the second conduit.

In one embodiment, distal ends of the first and second conduits are disposed on a second rotor that is operably connected to the first rotor for rotation relative to the first rotor from a first configuration in which the first conduit is aligned with the tissue disintegration module to a second configuration in which the second conduit is aligned with the tissue disintegration module. In one embodiment, the rotor has first and second apertures in fluid communication with the first and second conduits. Thus, rotation of the first rotor relative to the second rotor typically allows the system alternate between a first conveying mode in which tissue core in the needle biopsy module is conveyed to the tissue disintegration module and a second conveying mode in which gaseous molecules generated in the tissue disintegration module are conveyed to the analyser module.

In one embodiment, the disintegration module comprises an inner support configured to receive a tissue core biopsy and convert at least a part of the tissue core biopsy into gaseous tissue molecules, and an outer gas impermeable chamber.

In one embodiment, the system comprises a fluid delivery module configured to deliver fluid through the needle biopsy module. In one embodiment the fluid is a gas. In one embodiment, the fluid is a liquid. In one embodiment, the fluid is a solvent. In one embodiment, the fluid is or comprises a catalyst. The fluid may be an anaesthetic or a pharmacologically active agent or an imaging fluid. In one embodiment, the fluid delivery module comprises a conduit configured to deliver fluid to the needle through the tissue disintegration module. In another embodiment, the fluid delivery module comprises a conduit configured to deliver fluid directly to the needle. IN one embodiment, the pharmaceutically active agent is an agent for the local treatment of benign or malignant conditions, for example a chemotherapeutic, immunotherapeutic, or a radiotherapy agent.

In one embodiment, the system comprises a localisation marker delivery module configured to deliver a localisation marker through the needle biopsy module. The marker may be a metallic marker, gel marker, or a programmable electronic marker detectable by any means including GPS, Bluetooth, or RF. In one embodiment, the localisation marker delivery module comprises a conduit configured to deliver a marker directly to the needle.

In one embodiment, the system comprises a treatment module configured to deliver a therapy to a local site in the body, for example by means of electrophoresis, laser therapy or ablation therapy.

In one embodiment, the system comprises a needle guidance module, optionally forming part of the needle biopsy module. Typically, the needle guidance module comprises a guidance part and an imaging part that calibrates the guidance part. Typically, the imaging part is selected from x-ray radiography, mammography, ultrasound, nuclear medicine, PET scan, PET CT scan, CT scan or MRI.

The invention also relates to a method of generating data relating to a tissue core biopsy obtained from a patient comprising a step of generating data relating to a tissue core biopsy obtained from the patient using a system of the invention.

In one embodiment, the invention relates to a method of detecting or identifying a tissue abnormality in a patient comprising a step of generating data relating to a tissue core biopsy obtained from the patient using a system of the invention, and correlating the data with the presence or absence, or identity of, a tissue abnormality in the patient.

In one embodiment, the invention relates to a method of determining cancer status in a patient comprising a step of generating data relating to a tissue core biopsy obtained from the patient using a system of the invention, and correlating the data with the patients cancer status.

The invention also relates to a core needle biopsy device comprising a needle biopsy module configured to obtain a tissue core from a locus within the body, and a tissue disintegration module operably connected to the needle biopsy module and configured to receive the tissue core from the needle punch module, convert at least a portion of the tissue core into gaseous tissue molecules, and optionally convey gaseous tissue molecules from the tissue disintegration module to an analyser.

In one embodiment, the core needle biopsy module includes a tissue core collection module. In one embodiment, the device is adjustable from a first configuration in which the tissue disintegration module is aligned with the core needle biopsy module for receipt of a tissue core therefrom and a second configuration in which the tissue core collection module is aligned with the core needle biopsy module for receipt of a tissue core therefrom.

In one embodiment, the tissue core collection module and the tissue disintegration module are provided on a first rotor configured for rotation from at least the first configuration to at least the second configuration.

The invention also provides a core needle biopsy kit comprising:
- a needle punch module configured to obtain a tissue core from a locus within the body;
- a tissue disintegration module configured for removable attachment to the needle punch module, the tissue disintegration module adapted to (a) receive a tissue core from the needle punch module when attached thereto, (b) convert at least a portion of the tissue core into gaseous tissue molecules, and optionally (c) convey gaseous tissue molecules from the tissue disintegration module to an analyser module; and
- a tissue collection module configured for removable attachment to the core needle biopsy module in place of the tissue disintegration module for collection of one or more tissue cores from the core needle biopsy module.

The core needle biopsy device or core needle biopsy kit may also include the conveying means described above in connection with the system of the invention.

BRIEF DESCRIPTION OF THE FIGURES

The invention will be more clearly understood from the following description of some embodiments thereof given by way of example only with reference to the following figures in which:

FIG. 6 is an illustration of a system similar to that of FIG. 5;

FIGS. 10 and 11 are illustrations of a core needle biopsy (CNB) device of the invention;

DETAILED DESCRIPTION OF THE INVENTION

Figure 1:
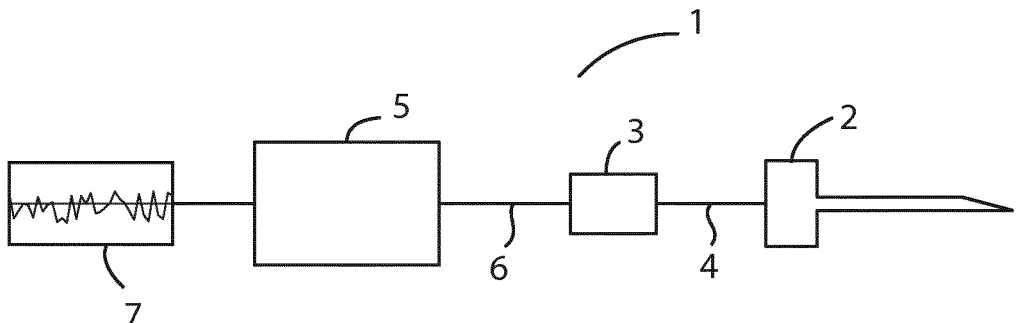
FIG. 1 is an illustration of a system for generating data relating to a tissue core according to a first embodiment of the invention.

The invention broadly provides a system for generating data relating to a tissue core comprising: a needle biopsy module configured to obtain a tissue core from a locus within the body; a tissue disintegration module operably connected to the needle biopsy module and configured to receive the tissue core from the needle biopsy module and convert at least a portion of the tissue core into gaseous tissue molecules; and optionally an analyser module operably connected to the disintegration module and configured to receive the gaseous tissue molecules from the disintegration module, analyse the gaseous tissue molecules, and generate data relating to the tissue core based on the gaseous tissue molecules.

Generally, the data collected relates to one or more constituents of the gaseous tissue molecules, which can be correlated with the presence or absence of chemicals and by measuring the mass-to-charge ratio and abundance of gas-phase ions as well as specific proteins, peptides, amino acids, metabolites, drugs, contaminants, microorganisms, etc. For example, the presence of certain metabolites can inform on the presence of a tissue abnormality, for example cancer or another disease. Methods of analysis of cellular tissue and biomolecules by mass spectrometry are described in US2011215233, US2007114375, U.S. Pat. No. 5,869,344, US2008149822 and WO2010136887. Methods for analysis of cellular tissue and biomolecules to detect cancer are described in Ocak et al (Proc Am Thorac Soc. 2009 6(2)); and Loo et al (Journal of the American Society for Mass Spectrometry Vol. 16, Issue 7, 2005).

When this system is employed to detect cancer (or other tissue related conditions), for every core that is disintegrated and analysed, it is generally necessary to take a duplicate core that is stored for cytological or histological analysis.

Thus, the system of the invention, or core needle biopsy device of the invention, preferably comprises a tissue core routing module having at least one core-receiving chamber and configured for adjustment to move the at least one chamber from a first position disposed to receive the core from the core needle biopsy module to one or more different positions. This allows the core to be routed to the disintegration chamber, or routed to an alternative module or destination.

The data collected may also relate to one or more constituents of the core needle biopsy tissue, which can be analysed by spectroscopy. For example, the core needle biopsy tissue or the products of denaturing can be analysed by spectroscopy or electromagnetic radiation for the presence of certain types of material such as atoms, molecules, crystals and nuclei. The presence of certain metabolites can inform on the presence of a tissue abnormality, for example cancer or another disease.

Typically, the system, or core needle biopsy device, of the invention further comprises a conveying module for conveying material within the system or device, for example the delivery of local anaesthetic to the biopsy site, tissue cores, cleaning, spraying or flushing material, or gaseous tissue molecules. In one embodiment, the conveying module comprises two, optionally separate, conveying sub-modules. In one embodiment, the conveying module comprises a vacuum pump module. Other conveying modules are also envisaged.

Typically, the conveying module is configured to (i) convey a tissue core biopsy from the needle punch module to another module, (ii) convey gaseous tissue molecules from the disintegration module to the analyser module, and/or (iii) flush leftover tissue from the disintegration module. When the system comprises a routing module, the conveying module is configured (i) convey a tissue core biopsy from the needle punch module to the routing module, (ii) convey a tissue core biopsy from the routing module to one or more modules, for example the disintegration module or a storage module, (iii) convey gaseous tissue molecules from the disintegration module to the analyser module, and/or (iiii) flush left over tissue from the disintegration module.

In another embodiment, the system or device of the invention comprises a flushing module configured to flush a part of the system or device (for example the disintegration module, routing module chamber, or the needle) with a flushing liquid to remove residual matter from the part of the system or device, especially blood and cells. In one embodiment, the flushing module is operatively connected to the disintegration chamber and configured to flush the chamber with a flushing liquid and remove the flushing liquid and contaminants from the chamber. In another embodiment, the flushing module is operatively connected to one or more tissue core receiving chambers of the routing chamber and configured to flush the or each chamber with a flushing liquid and remove the flushing liquid and contaminants from the chamber. The flushing liquid may include but is not limited to distilled water, saline, a catalyst solution or a dilute formaldehyde solution. Suitably, the flushing module comprises a reservoir of flushing fluid, pump means, and conduit means operatively connected to the reservoir and pump means and configured to pump flushing liquid from the reservoir to a chamber of the system (for example the denaturation module or a chamber of the routing module or the needle).

Typically, the needle punch module is a core biopsy needle punch (used in core needle biopsy (CNB) procedures, stereotactic CNB procedures, and vacuum assisted core biopsy procedures). The needle punch module generally comprises a tissue core conduit adapted to convey a tissue core from lumen of the needle to the disintegration module or the routing module. Typically, the tissue core is conveyed by vacuum.

Suitably, the disintegration module is configured to ionize all or part of the tissue core. Typically, the disintegration module comprises an inner chamber configured to receive a tissue core and convert at least a part of the tissue core into gaseous tissue molecules, an outer chamber that embraces the inner chamber, and a conduit providing fluid communication between the outer chamber and the analyser module, wherein the inner chamber comprises a plurality of apertures configured to allow passage of gaseous tissue molecules from the inner chamber to the outer chamber. Preferably, the inner chamber comprises a tray adapted to hold the tissue core, or a cylinder configured to contain the tissue core.

Suitably, the inner chamber comprises a tissue disintegration element, for example a heating element. Preferably, the inner chamber is at least partly formed of a braided heating element.

Suitably, the analyser comprises a mass spectrometer optionally in combination with a data processor configured to receive data from the mass spectrometer and process the data. The analyser may also comprise a data storage module, and a data comparison module configured to compare data received from the mass spectrometer or data storage module with reference data. In one embodiment, the analyser comprises communication means configured to send data generated by the mass spectrometer to a remote location for storage or data processing via any electronic communication means including but not limited to Bluetooth, SMS messaging or via the internet.

The invention also provides a method of analysing tissue obtained from a patient comprising a step of generating data relating to a tissue core obtained from the patient using a system of the invention, and analysing the data. The analysis may be for the purpose of detecting (qualitatively or quantitatively) (a) an abnormality with the tissue (b) the presence of a particular metabolite in the tissue, (c) the presence of a microbial contaminant in the tissue (d) the presence of a drug or drug metabolite in the tissue. The abnormality to be detected may include a disease selected from a malignancy (cancer or a metastasis thereof), a metabolic disease, an inflammatory disease, an autoimmune disease, or a neurodegenerative disease. Examples of cancer are provided below. In a preferred embodiment, the analysis involves detecting cancer, especially bone, breast cancer, gynaecological, liver, lung cancer, lymphoproliferative cancer, prostate, renal, thyroid or a metastasis thereof. The analysis may involve comparing the patient-specific data with reference data to detect a particular chemical, phenotype, disease, condition, compound, molecule, or contaminant. In one embodiment, the analysis comprises generating a mass spectrometer fingerprint from the tissue core data, and comparing the mass spectrometer fingerprint with at least one reference fingerprint. Comparison may be visual, or performed by means of computer implemented comparison software.

Definitions

"Tissue core" means a core or plug of tissue obtained from within the body using core needle biopsy device. Generally, the core is cylindrical is shape and has a length of 1-2 cm and a width of 0.1 to 0.5 cm.

"Core needle biopsy module" or "core needle biopsy device" or "CNB" means a hand-held or robotically-controlled instrument comprising a needle punch capable of obtaining a tissue core from a locus inside the body in a minimally invasive manner. In particular, the term should be understood to mean core needle biopsy devices that employ vacuum means to sequester a core of tissue and withdraw the core of tissue through a lumen within the needle. Examples of CNB devices are described in Brun del Re et al, Minimally Invasive Breast Biopsies, Recent Results in Cancer Research 173, Springer (ISBN 978-3-540-31403-5), especially the article entitled "Comparison of Large-Core Vacuum-Assisted Breast and Biopsy Excision Systems (Robert Wilson, Pages 23-41).

"Needle punch" means the type of needle employed in CNB devices and generally comprises a needle capable of being actuated to sequester a core of tissue from a locus inside the body. In one embodiment, the needle punch is of the type having an internal retractable sheath that can be actuated to withdraw and retract to excise a core of tissue sequestered into the core of the needle.

"Locus within the body" means a location within the body that can be accessed in a minimally invasive manner using a CNB device. Examples of suitable loci including but not limited to breast tissue, lung tissue, liver tissue, other organ tissues, lymph tissue, prostate tissue, gastrointestinal tissue, and respiratory tract tissue.

"Tissue disintegration module" means a device capable of receiving a tissue core and treating the core to convert at least a part, and preferably substantially all, of the tissue core to gaseous tissue molecules (i.e. ionize all or part of the tissue). The module may comprise a heating element that ionises the tissue, for example a thermocouple or a chamber or tray formed of or comprising heating elements or filaments.

"Analyser module" means an analysis system that can receive gaseous tissue molecules and perform a qualitative analysis of the molecules. Generally, the module comprises a mass spectrometer (MS), for example a MALDI-TOF MS, accelerator MS, Tandem MS, thermal ionisation MS (TIMS), and spark source MS (SSMS). Further examples of analyser and MS configurations suitable for the present invention are described in WO2010136887.

"Data relating to the tissue core" generally means data relating to the presence, absence, or absolute or relative amounts of one or more components, for example chemicals, proteins, peptides, amino acids, metabolites, drugs, drug metabolites, microorganisms, and components of microorganisms.

"Tissue core routing module" means a device having at least one core-receiving chamber and is configured for adjustment to move the at least one chamber from a first position disposed to receive the core from the core needle biopsy module to one or more different positions (for example at least 2, 3, 4, 5, 6, or 7 different positions). Preferably, the routing module is configured to perform at least two of the following functions: store the core; convey the core to the tissue disintegration module; and convey the core to a core collection module. Preferably, the routing module is adjustable to move the at least one chamber from the first position to a second position disposed to deliver the core to the core disintegration module or a core collection module. In one embodiment, the core routing module comprises a plurality of core-receiving chambers, for example at least 3, 4, 5, 6, 7, or 8 chambers.

"Tissue core collection module" means a chamber operatively connected with the routing module and adapted to receive and hold tissue cores from the routing module. In a preferred embodiment it is attached to the routing module. Ideally, it is detachable attached to the routing module.

"Tissue abnormality" means a non-normal tissue phenotype, for example diseased tissue. Examples of tissue abnormalities include benign and malignant tissue, inflammation, and infected tissue. The tissue abnormality may be solid, cystic or part solid-cystic. Tissue malignancies include cancer, for example primary cancer and metastases thereof. Generally, a cancer is a solid tumor. Examples of tumors are solid tumors of the Chest (chest wall and pleura, mediastinum, lungs), Gastrointestinal (Oesophagus, stomach, duodenum, small bowel colon, liver biliary, pancreas, spleen, peritoneum, mesentery and omentum), Genitourinary (kidneys, bladder, prostate, urethra, male reproductive system), Musculoskeletal (bone tumours), Gynaecological, Breast, Neuroradiology. Endocrine tumours and lymphoma and others.

"Metabolite" means a product of the eukaryotic or prokaryotic metabolism including amino acids, chemicals, sugars, fatty acids, and precursors or derivatives thereof.

"Microbial contaminant" includes a bacteria, virus or fungus, or a component or metabolite thereof.

"Drug" means a pharmaceutically active agent indicated for the prevention or treatment of disease or conditions in mammals. "Drug metabolite" means a break-down product of the drug as a result of the drug being metabolised in a mammal.

"Hand-held" as applied to the core needle biopsy device means that the device is adapted to held by a user during use in a core needle biopsy procedure.

Referring to the drawings, and initially to FIG. 1, there is illustrated a system for generating data relating to a tissue core according to a first embodiment of the invention, and indicated generally by the reference numeral 1. The system 1 comprises a core needle biopsy (CNB) module 2, a tissue disintegration module 3 operatively connected to the CNB module 2 by means of a conduit 4, and a mass spectrometer 5 in fluid communication with the tissue disintegration module 3 by means of a conduit 6. In use, the CNB module is employed to obtain a tissue core from a patient and deliver the tissue core to the tissue disintegrator 3 where the tissue core is converted to gaseous tissue molecules by heating. The gaseous tissue molecules are then conveyed to the mass spectrometer 5 and analysed by the mass spectrometer to generate tissue specific data 7.

Figure 2:
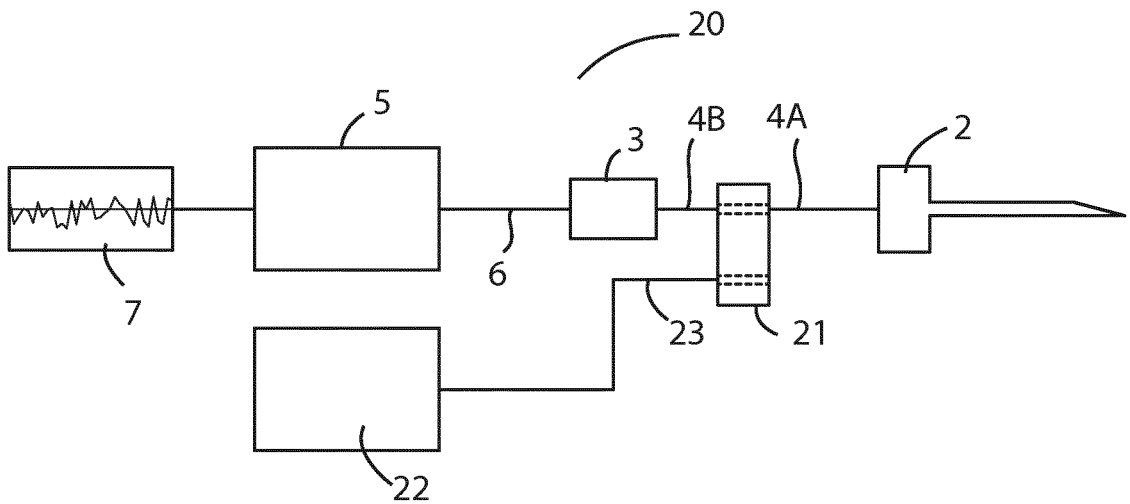
FIG. 2 is an illustration of a system for generating data relating to a tissue core according to a second embodiment of the invention, having a routing module and tissue core collection module.

Referring to FIG. 2 an alternative embodiment of the system of the invention is shown, indicated generally by the reference numeral 20, in which parts described with reference to the previous embodiment are assigned the same reference numerals. In this embodiment, the system comprises a rotor 21 and a tissue core collection module 22, both of which are located remotely to the CNB module 2. The rotor 21 comprises a revolving cylinder having a tissue core receiving chamber (not shown) that is movable from a first position where it aligns with conduits 4A and 4B (thus allowing the a tissue core be conveyed from the biopsy module 2 to the disintegration chamber 5 via conduit 6) to a second position where the tissue core chamber aligns with conduit 23 leading to the core collection chamber. The use of this embodiment is the same as that described in relation to FIG. 1 except that the rotor can be actuated to route tissue cores either to the disintegration module or to the collection module. In practice, for every core that is disintegrated a duplicate core will need to be stored.

Figure 3:
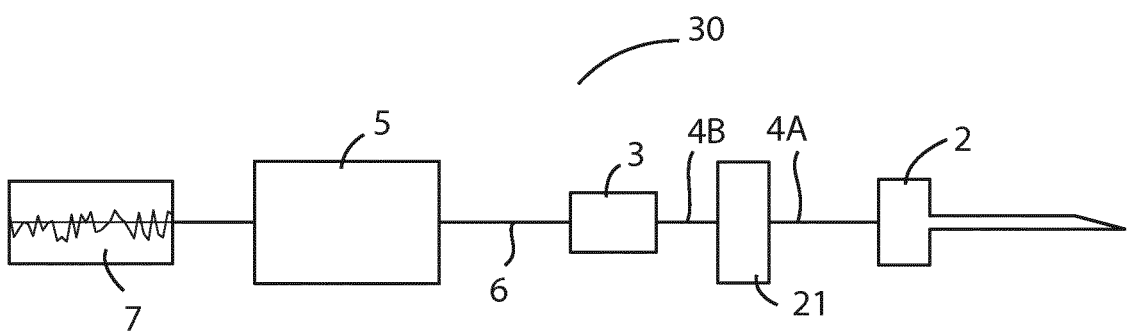
FIG. 3 is an illustration of a system for generating data relating to a tissue core according to a third embodiment of the invention, having a routing module that incorporates a storage function.

Referring to FIG. 3 an alternative embodiment of the system of the invention is shown, indicated generally by the reference numeral 30, in which parts described with reference to the previous embodiments are assigned the same reference numerals. In this embodiment, the rotor 21 comprises a rotating cylinder having a four tissue core receiving chambers (not shown, but see FIG. 6) and is capable of holding up to four cores at any one time. In use, every second core received by the rotor is routed to the disintegration module 3 and the remaining cores are held/collected within the rotor and eventually removed for further analysis (histological or cytological).

Figure 4A:
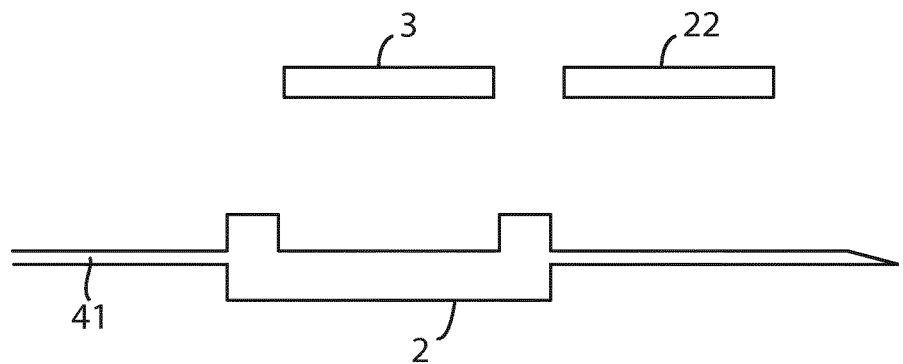
FIG. 4 is an illustration of a "plug-and-play" system of the invention including separate collection and disintegration modules configured for removable attachment to the needle biopsy module.
Figure 4B:
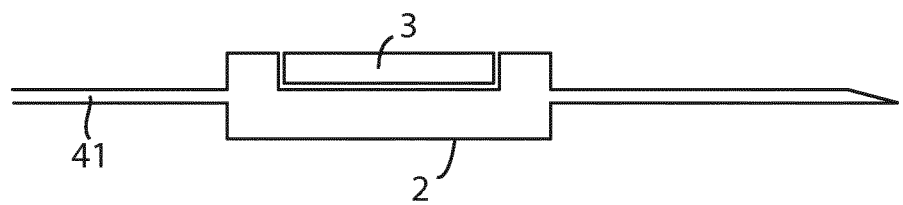
Figure 4C:
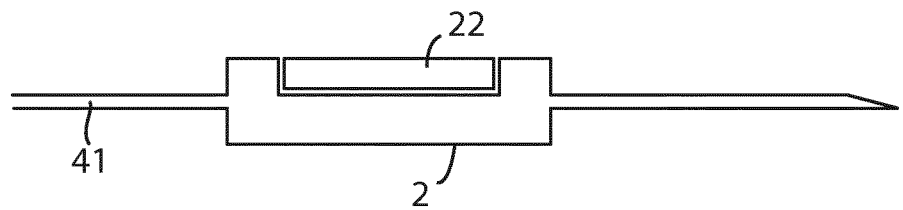

Referring to FIG. 4 a "plug-and-play" embodiment of the system of the invention is illustrated and comprises a CNB module 2 and separate tissue disintegration module 3 and core collection module 22 which are configured for removable attachment to the CNB module 2 (FIG. 4A). In FIG. 4B, the system is shown with the tissue disintegration module 3 in-situ whereby cores obtained by the CNB module are withdrawn into the disintegration module 3 by means of a vacuum generated through a conduit 41. In FIG. 4C, the system is shown in core collection mode with the disintegration module 3 removed and replaced with the core collection module 22.

Figure 4D:
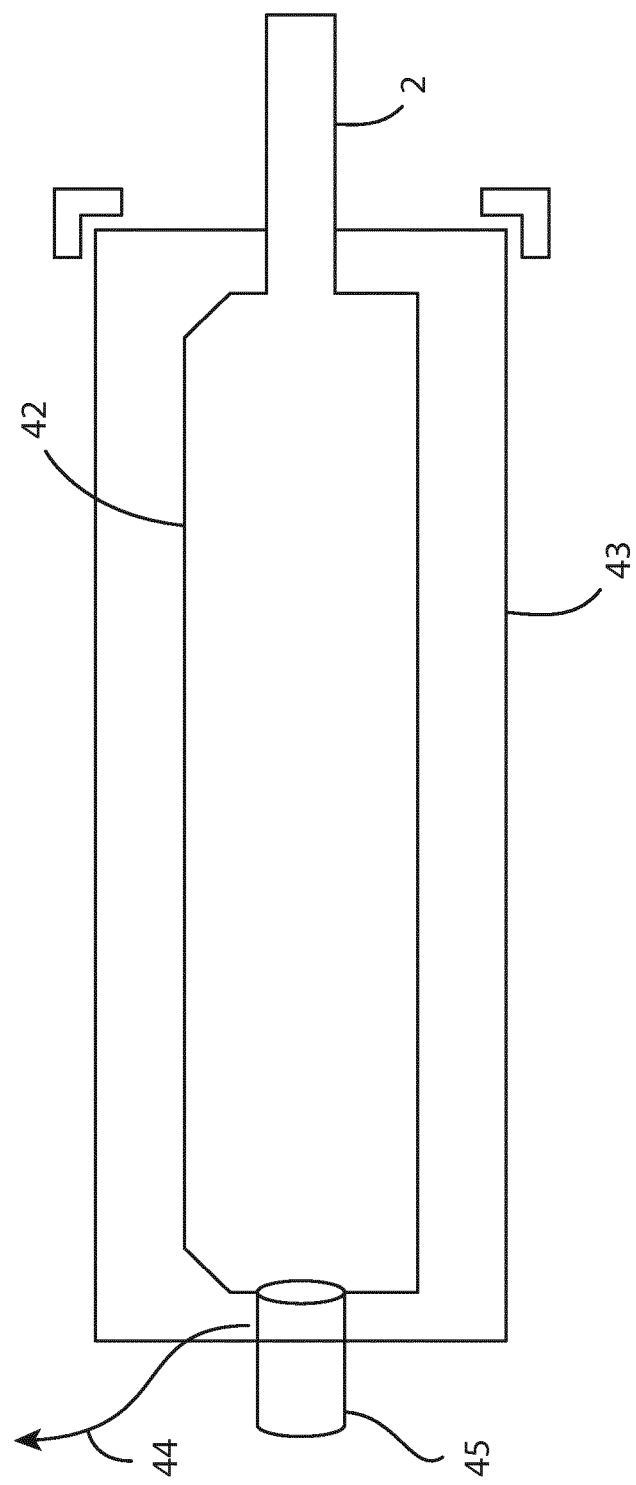

Referring to FIG. 4D, the core collection module is illustrated in more detail and comprises an inner chamber 42 configured to operably connect with the CNB device 2 for receipt of a tissue core from the CNB device, and an outer chamber 43 connected to a vacuum pump conduit 44 for removal of excess fluids from the outer chamber. A distal end of the inner chamber 42 comprises a system of connectors 45 configured to deliver a flushing fluid to the inner chamber, and optionally to deliver other fluids (for example anaesthetic, catalyst, solvent) or a localisation marker to the inner chamber.

Figure 4E:
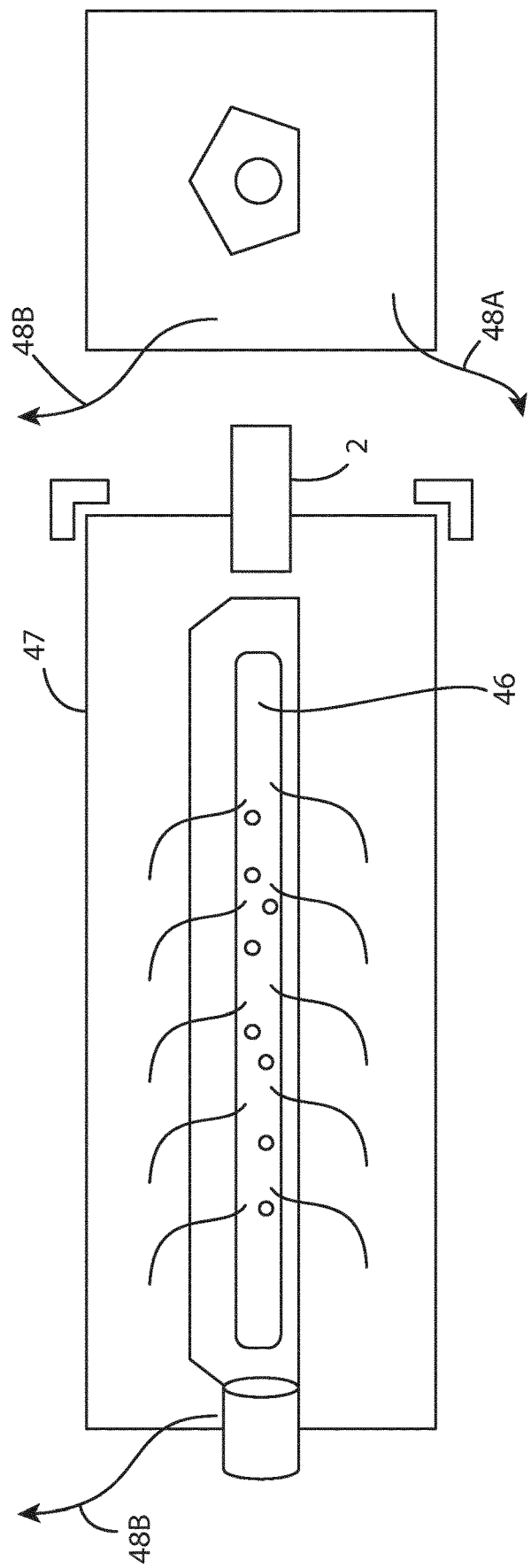

Referring to FIG. 4E, the tissue disintegration module is shown in more detail and comprises an inner chamber/thermocouple 46 that is aligned with the CNB device 2 for receipt of a tissue core from the CNB device, and an outer chamber 47 connected to a vacuum pump conduit 48A for removal of excess fluids from the outer chamber or a vacuum pump conduit 48B for removal of gaseous molecules to an analyser module (not shown). A distal end of the inner chamber 46 comprises a connector 49 configured to deliver a flushing fluid to the inner chamber. The inner chamber/thermocouple 46 is connected to an electrical supply allowing the thermocouple disintegrate a tissue core contained within the thermocouple. The thermocouple is perforated with holes allowing gaseous molecules pass into the outer chamber where they are removed by vacuum to the analyser.

Figure 5A:
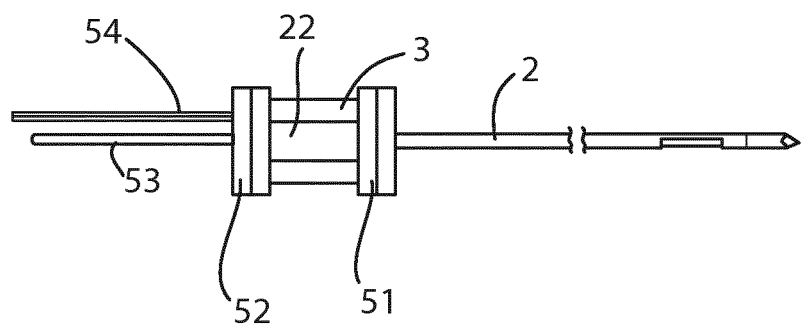
FIG. 5 shows a series of illustrations of a system according to the invention including a needle biopsy module, disintegration module and core collection module formed as a single, adjustable unit.
Figure 5B:
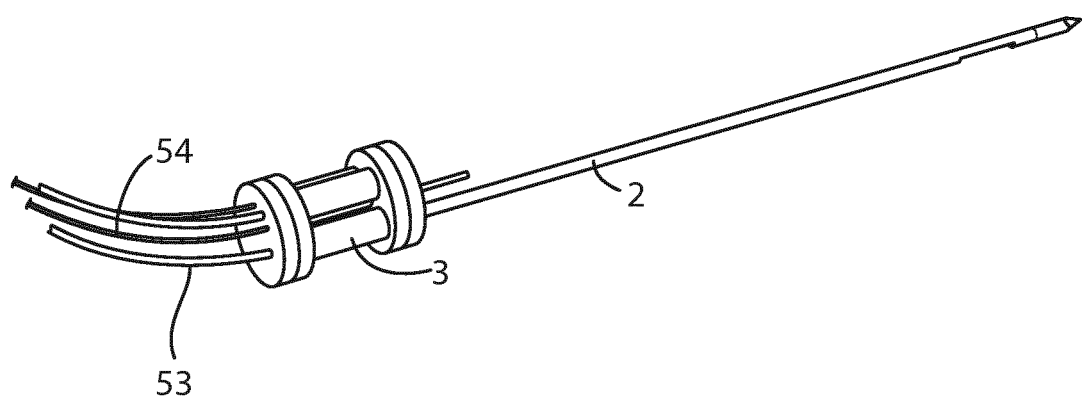
Figure 5C:
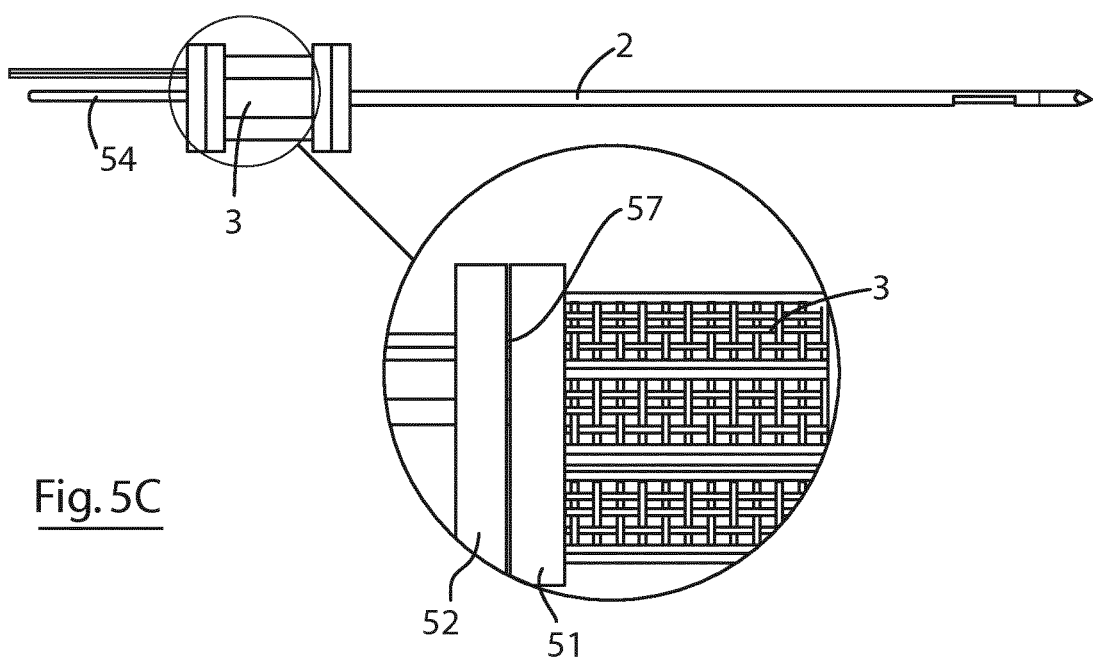

Referring to FIG. 5, there is illustrated an embodiment of the system having a CNB device 2, tissue disintegration module 3, and core collection module 22 provided as a single unit. In this embodiment, the tissue disintegration module 3 and core collection module 22 are provided on a first rotor 51 configured for rotation relative to the CNB device 2 between a number of different configurations. The unit also includes a second rotor 52 operably connected to a purging vacuum conduit 53 and a gaseous molecule extraction conduit 54. In a first configuration shown in FIG. 5A, the core collection chamber 22 is aligned with the CNB device 2 and the purging vacuum conduit 53 such that a first tissue core is extracted from a site and captured in the collection chamber. All impurities are vacuumed from the sample and it is retained within the chamber until the sampling process is complete. In a second configuration shown in FIG. 5B, the rotors 51 and 52 have rotated to align the CNB device 2 with the tissue disintegration module 3 and the purging vacuum conduit 53 resulting in a second tissue core being extracted and delivered to the disintegration module 3. The first tissue core in the collection chamber 22 is now aligned with the gaseous molecule extraction conduit 54. In the third configuration shown in FIG. 5C, the rotor 51 is rotated such that the disintegration module 3 is aligned with the gaseous molecule extraction conduit 54. As shown in FIG. 4D, electrical terminals 57 on the disintegration module 3 establish electrical connection with corresponding terminals on the second rotor 52 causing the tissue disintegration module to actuate and disintegrate the tissue core whereby gaseous molecules generated are withdrawn to an analyser for analysis.

Referring to FIG. 6, there is illustrated a further embodiment of the system shown in FIG. 5 in which parts identified with reference to the previous embodiment are assigned the same reference numerals. In this embodiment the tissue disintegration module 2 and core collection module 22 mounted on the rotor 51 are contained within an outer chamber 60 connected to a purging vacuum through conduit 62. A conduit 63 is connected to the collection module 22 for the purpose of flushing the module with a flushing fluid and a similar conduit 64 is connected to the disintegration module 2 for the purpose of flushing the module 2. A further conduit 65 provides fluid connection between the outer chamber 60 and the analyser (not shown). A distal end of the outer chamber 60 comprises a system of connectors 66 configured to deliver a flushing fluid to the inner chamber, and optionally to deliver other fluids (for example anaesthetic, catalyst, solvent) or a localisation marker to the inner chamber.

Figure 7:
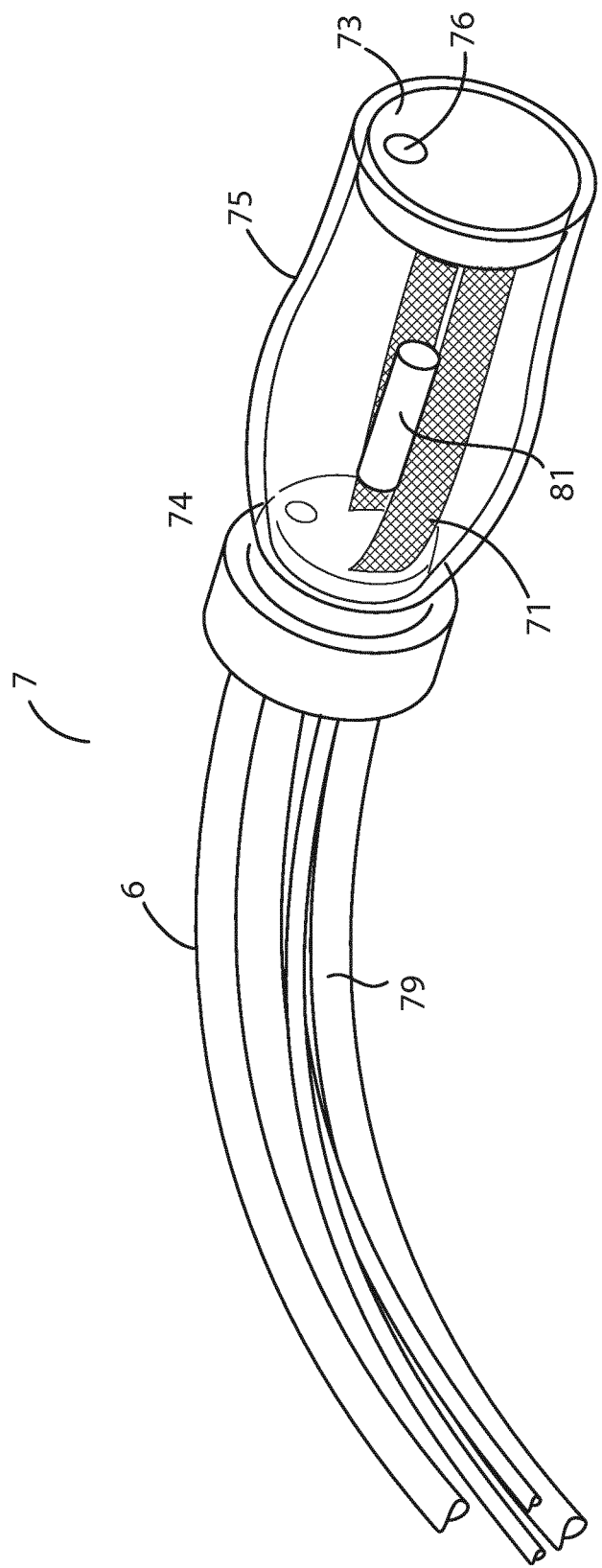
FIG. 7 is an illustration of a disintegration module forming part of the system or device of the invention.
Figure 8:
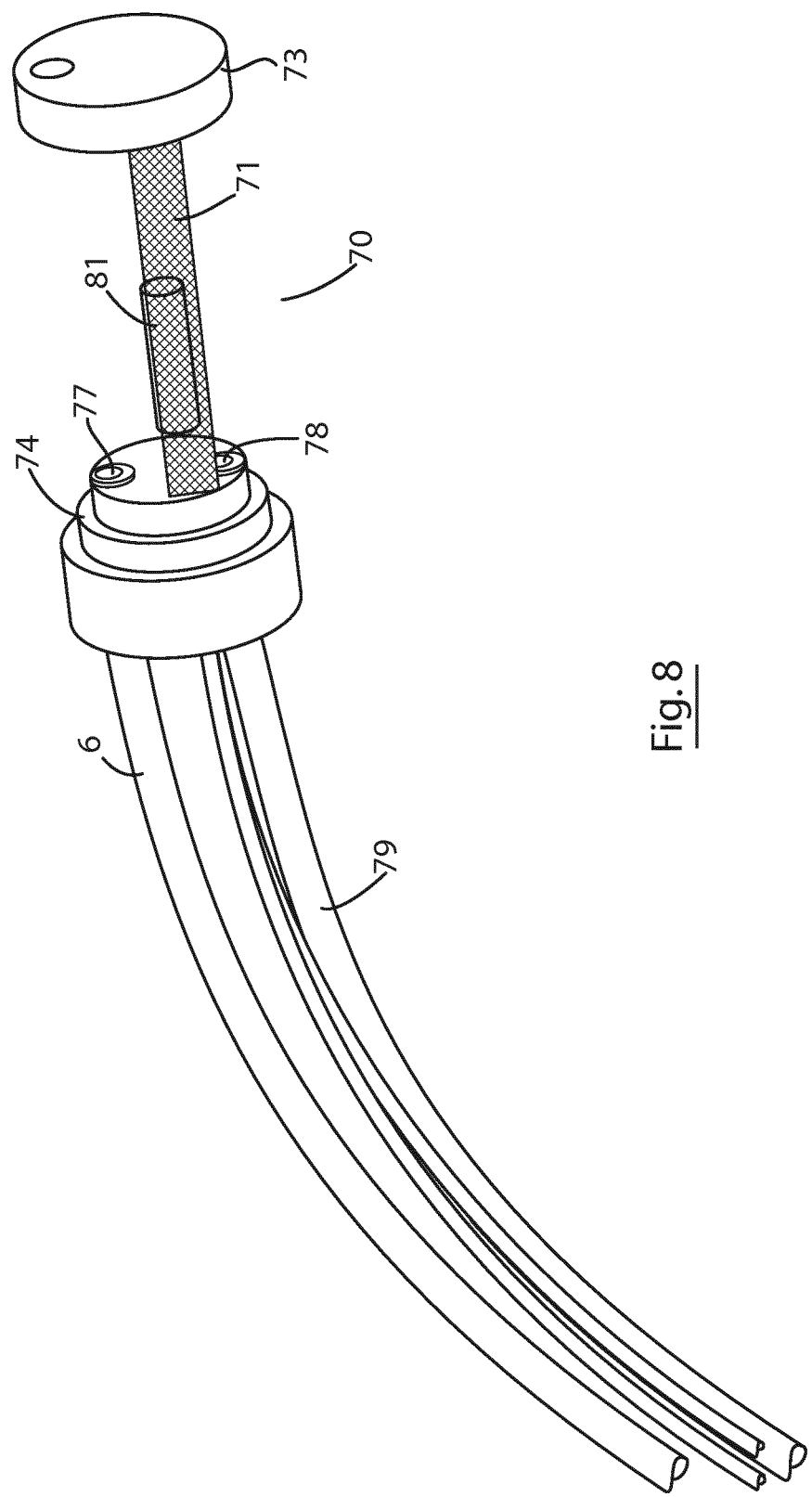
FIG. 8 is an illustration of the disintegration module of FIG. 7 with the outer chamber removed.

Referring to FIGS. 7 and 8 these is illustrated a disintegration module forming part of the system or device of the invention, indicated generally by the reference numeral 70 and comprising an inner chamber (in this case a tray 71 formed of a braided heating element), and an outer chamber comprising insulated ends 73, 74 and an insulated heat resistant glass tube 75. The distal end 73 comprises an aperture 76 configured for engagement with conduit 4A leading to the CNB device 2. The proximal end 74 comprises a aperture 77 in fluid communication with a conduit 6 leading to the analyser module 5, and a second aperture 78 in fluid communication with a vacuum pump (not shown) via conduit 79 for the purpose of pressuring the system and conveying tissue cores from the CNB device and routing module to the disintegration module 70. Valves are associated with both of apertures 73 and 74 and the valve associated with aperture 74 is configured to open when a vacuum is applied downstream of the valves. In use, a vacuum pump (not shown) is actuated to apply a negative pressure in conduit 79 causing the valve in aperture 74 to open and depressurisation of the disintegration module 70 and conduit 4A. This results in the tissue core in conduit 4A being drawn into the module 70 and falling onto the tray 71. Valves are then closed and the heating element is actuated to ionize the tissue core 81 and gaseous tissue is withdrawn to an analyser 5 via the conduit 6.

Figure 9:
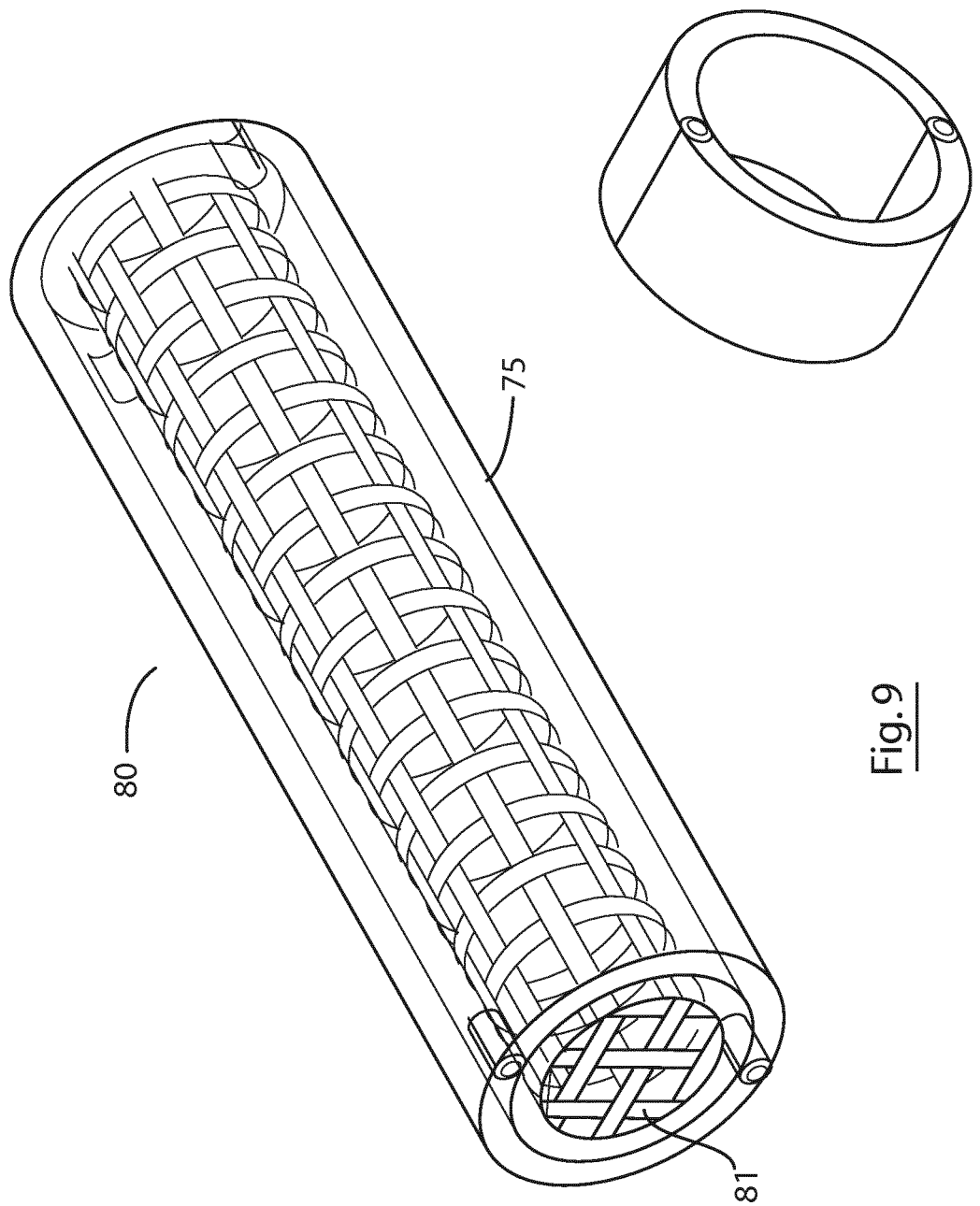
FIG. 9 is an illustration of an alternative design of disintegration module forming part of the system or device of the invention.

FIG. 9 illustrates an alternative embodiment of the disintegration module (80) in which the inner chamber comprises a tray 81 formed of braided heating filaments.

FIGS. 10 and 11 illustrate a core needle biopsy (CNB) device 90 comprising a needle punch module 91 configured to obtain a tissue core from a locus within the body, and a tissue disintegration module 70 (as described previously) operably connected to the needle punch module and configured to receive the tissue core from the needle punch module and convert at least a portion of the tissue core into gaseous tissue molecules. The use of this device is the same as that described previously.

In practice, the CNB device is for use within a hospital or clinic setting. The device is for use on benign and malignant appearing tissues. The tissue abnormality maybe non palpable or palpable. The CNB device for use under image guidance may be by free hand or by use of stereotactic guidance. If the area is easily felt, the biopsy needle may be guided into the tumor while feeling (palpating) the lump. The CNB device is generally for use with image guidance. Image guidance devices consist of a number of modalities. The image modality to guide the CNB device includes but is not limited to x-ray radiography, mammography, ultrasound, nuclear medicine, PET scan, PET CT scan, CT scan or MRI. The CNB image device is calibrated to the imaging modality.

The tissue abnormality, generally appears as an image of the tissue on an imaging modality device. The tissue abnormality may be evident on one imaging modality but not on another. Local anaesthetic is injected into the skin where the CNB device is to be inserted. The CNB device is inserted using image guidance into the tissue abnormality using one of the above imaging modalities. Local anaesthetic in instilled via a port into the locus of the biopsy site using the CNB device.

During the CNB procedure, the hollow CNB device is used to withdraw small cylinders (or cores) of tissue from the abnormal area within the breast. A CNB is most often done in a doctor's office with local anesthesia. The needle is put into the abnormal tissue to get the samples, or cores. The doctor doing the CNB usually places the needle in the abnormal area using ultrasound or x-rays to guide the needle into the right place.

A stereotactic core needle biopsy uses x-ray equipment and a computer to analyze pictures of the breast. The computer then pinpoints exactly where in the abnormal area the needle tip needs to go. This is often done to biopsy suspicious microcalcifications (tiny calcium deposits) when a tumor cannot be felt or seen on ultrasound.

Vacuum-assisted biopsies can be done with systems like the Mammotome® or ATEC® (Automated Tissue Excision and Collection). For these procedures, the skin is numbed and a small cut (less than ¼ inch) is made. A hollow probe is put in through the cut and guided into the abnormal area of breast tissue using x-rays, ultrasound, or MRI. A cylinder of tissue is then pulled into the probe through a hole in its side, and a rotating knife inside the probe cuts the tissue sample from the rest of the breast.

These methods allow multiple tissue samples to be removed through one small opening. They are also able to remove more tissue than a standard core biopsy. Vacuum-assisted core biopsies are done in outpatient settings.

A Magnetic resonance imaging (MRI) guided biopsy guides the biopsy. For instance, with the ATEC system, you lay face down on a special table with an opening that your breast fits into. Computers are then used to find the tumor, plot its location, and help aim the probe into the tumor. This is helpful for women with a suspicious area that can only be found by MRI.

The CNB device consists of a port to permit the insertion of a localization marker at the site of the core needle biopsy. The device may include but is not limited to metallic, gel or programmable electronic markers. All of the above tissue localization markers can be detected by one of the following x-ray radiography, mammography, ultrasound, nuclear medicine, PET scan, PET CT scan, CT scan or MRI. The localisation markers listed above are compatible and safe to use with all of the above imaging modalities.

The invention is not limited to the embodiments hereinbefore described which may be varied in construction and detail without departing from the spirit of the invention.

The invention claimed is:

1. A system for generating data relating to a tissue core, comprising:
    a core needle biopsy module configured to obtain a tissue core from a locus within a patient's body;
    a tissue disintegration module operably connected to the core needle biopsy module and configured to receive the tissue core from the core needle biopsy module and convert at least a portion of the tissue core into gaseous tissue molecules or ions;
    a first vacuum pump configured to convey the tissue core from the core needle biopsy module to the tissue disintegration module;
    a second vacuum pump configured to convey gaseous tissue molecules or ions from the tissue disintegration module to an analyser module, and
    a tissue core collection module, wherein the tissue disintegration module, the core needle biopsy module, and the tissue core collection module are provided as a single unit, the single unit being adjustable from a first configuration in which the tissue disintegration module is aligned with the core needle biopsy module for receipt of a tissue core therefrom and a second configuration in which the tissue core collection module is aligned with the core needle biopsy module for receipt of a tissue core therefrom.

2. A system as claimed in claim 1, further comprising an analyser module operably connected to the second vacuum pump for receipt of the gaseous tissue molecules or ions from the tissue disintegration module, and configured to analyse the gaseous tissue molecules or ions, and generate data relating to the tissue core based on the gaseous tissue molecules or ions.

3. A system as claimed in claim 2, wherein the analyser module comprises a mass spectrometer.

4. A system as claimed in claim 1, wherein the tissue disintegration module is removably attached to the core needle biopsy module.

5. A system as claimed in claim 4, wherein the tissue core collection module is removably attached to the core needle biopsy module.

6. A system as claimed in claim 1, wherein the tissue core collection module and the tissue disintegration module are provided on a first rotor configured for rotation from at least the first configuration to at least the second configuration.

7. A system as claimed in claim 6, wherein the first vacuum pump and second vacuum pump are provided on a second rotor that is operably connected to the first rotor for rotation relative to the first rotor from a first configuration in which the first vacuum pump is aligned with the tissue disintegration module to a second configuration in which the second vacuum pump is aligned with the tissue disintegration module.

8. A system as claimed in claim 1, wherein the tissue disintegration module comprises an inner support configured to receive a tissue core biopsy and convert at least a part of the tissue core biopsy into gaseous tissue molecules or ions, an outer gas impermeable chamber, and an outlet conduit in fluid communication with the second vacuum pump.

9. A system as claimed in claim 1, further comprising means for delivering an active agent or a localisation marker to a locus within the patient's body.

* * * * *